(12) United States Patent
Nasser et al.

(10) Patent No.: US 8,455,696 B2
(45) Date of Patent: Jun. 4, 2013

(54) OPTIMIZED PRODUCTION OF KETONES/ALDEHYDES

(75) Inventors: Roberto Nasser, Sao Paulo (BR); Dalva Janine Rita, Campinas (BR); Joël Schwartz, Caluire (FR)

(73) Assignee: Rhodia Poliamida E Especialidades LTDA, Sao Paulo (BR)

( * ) Notice: Subject to any disclaimer, the term of this patent is extended or adjusted under 35 U.S.C. 154(b) by 175 days.

(21) Appl. No.: 12/989,204

(22) PCT Filed: Apr. 22, 2009

(86) PCT No.: PCT/EP2009/054825
§ 371 (c)(1),
(2), (4) Date: Oct. 22, 2010

(87) PCT Pub. No.: WO2009/130245
PCT Pub. Date: Oct. 29, 2009

(65) Prior Publication Data
US 2011/0040128 A1    Feb. 17, 2011

(30) Foreign Application Priority Data
Apr. 23, 2008   (FR) ..................................... 08 02271

(51) Int. Cl.
*C07C 45/61*   (2006.01)
*B01J 19/00*   (2006.01)

(52) U.S. Cl.
USPC ............................ 568/388; 568/458; 422/234

(58) Field of Classification Search
USPC .................................. 568/388, 458; 422/234
See application file for complete search history.

(56) References Cited

U.S. PATENT DOCUMENTS

| 4,910,344 A | 3/1990 | Pasternak et al. |
| 6,960,694 B2 | 11/2005 | Barnicki et al. |

OTHER PUBLICATIONS

Staudt-Bickel et al. Integration of pervaporation for the removal of water in the production of methyl isobutyl ketone. Journal of Membrane Science, 1996, vol. 111, 135-141.*
International Search Report corresponding to PCT/EP 2009/054825.

* cited by examiner

*Primary Examiner* — Sikarl Witherspoon
(74) *Attorney, Agent, or Firm* — Dentons US LLP

(57) ABSTRACT

Production of a ketone or aldehyde prepared by condensation is optimized by dehydration and hydrogenation of a starting acetone/ketone or aldehyde in a reaction zone and wherein water is partially eliminated from such reaction product by at least one membrane pervaporation module, the pervaporation module being fed tangentially and situated laterally to the reaction zone and operating in a loop, and wherein a fraction of reaction product exiting the reaction zone is thus partially dehydrated and recycling such dehydrated concentrate to the reaction zone.

15 Claims, 1 Drawing Sheet

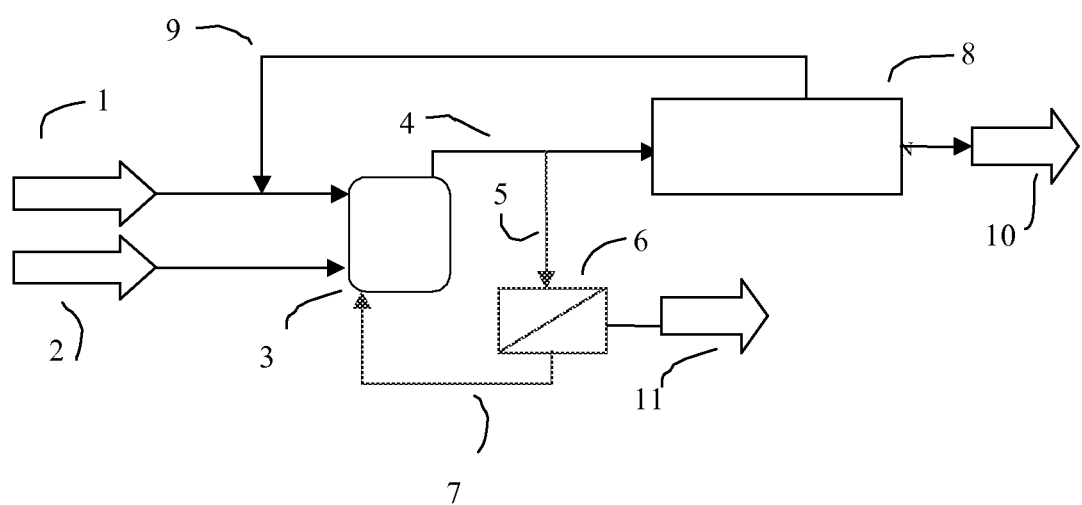

OPTIMIZED PRODUCTION OF KETONES/ALDEHYDES

CROSS-REFERENCE TO PRIORITY/PCT EARLIER APPLICATIONS

This application is a U.S. national stage of PCT/EP 2009/054825, filed Apr. 22, 2009 and designating the United States (published in the French language on Oct. 29, 2009, as WO 2009/130245 A1, the title and abstract were also published in English); which claims foreign priority under 35 U.S.C. 119 of FR 0802271, filed Apr. 23, 2008, each hereby expressly incorporated by reference in its entirety and each assigned to the assignee hereof.

The process according to the invention targets the optimization of the production of ketones or of aldehydes obtained by condensation followed by dehydration and hydrogenation of the ketones or aldehydes in a reactor (3), by carrying out a membrane pervaporation step (6) that makes it possible to partially dehydrate a fraction (5) exiting the reactor and to recycle the dehydrated concentrate (7) to said reactor (3).

Schematically, the mechanism of reaction for obtaining ketones or aldehydes of higher mass can be represented by elementary reactions; for example with regard to methyl isobutyl ketone (MIBK):

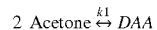
2 Acetone $\overset{k1}{\leftrightarrow}$ DAA

DAA $\overset{k2}{\leftrightarrow}$ OM + H$_2$O

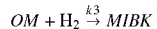
OM + H$_2$ $\overset{k3}{\rightarrow}$ MIBK or else by the overall reaction:

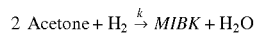
2 Acetone + H$_2$ $\overset{k}{\rightarrow}$ MIBK + H$_2$O

What should be taken from the mechanisms presented is the fact that the reactions involve constitute pseudo-equilibria, in which the degree of conversion of the acetone depends on the concentration of water in the reaction mass, as indicated below:

$$\frac{dm_{MIBK}}{d\theta} = \frac{W}{V} \cdot K \cdot P_{PH_2} \cdot \frac{x^2_{acetone}}{x_{H_2O}}$$

where:

$$\frac{dm_{MIBK}}{d\theta}$$

represents the degree of formation of MIBK;

$$\frac{W}{V}$$

represents the mass of catalyst;
K—characteristic constant of the system;
$P_{PH_2}$—represents the hydrogen partial pressure;
$x_{acetone}$—represents the molar fraction of acetone;
$x_{H_2O}$—represents the molar fraction of water.

In other words, the lower the water content of the reaction mass, the greater the conversion, and vice-versa.

The reactor operates at a temperature of between 50 and 150° C. and at a pressure of between 500 and 2000 kPa, and the water concentration at the output of the reactor is about 3% to 5% by weight.

The output of the reactor conventionally feeds a set of columns, in which the MIBK is purified, and which separate it from the acetone, which returns to the reaction.

The object of the present invention is to develop a novel process for producing ketones or aldehydes, for example MIBK, by reducing the concentration of water in the reaction medium by approximately 1% by weight, in order to obtain a shift in the equilibrium toward the side of the product and thus an increased reaction yield, an increase in productivity, and an energy saving.

It has been possible to obtain such properties by using, in a process for obtaining ketones or aldehydes obtained by condensation followed by dehydration and hydrogenation of ketones or aldehydes in a reactor, a loop that makes it possible to recover a fraction exiting the reactor, comprising, for example, a mixture of water, acetone and MIBK in the case of the production of MIBK, in order to convey it to a membrane pervaporation module so as to partially dehydrate it and then to send it back to said reactor.

Specifically, it appears, entirely surprisingly, that even a partial dehydration of the reaction medium made it possible to obtain an increased reaction yield and a large increase in ketone or aldehyde productivity.

The partial dehydration of the reaction mass by approximately 1% by weight shifts the equilibrium of any pseudo-equilibrium reaction toward the side of the formation of the product; this increases the reaction yield and therefore the productivity of the system, and, consequently, results in an energy saving, which is not limited only to the production of MIBK, but can be extended to other products obtained by means of similar pseudo-equilibrium reactions, for instance butanal, obtained from acetaldehyde.

Membrane pervaporation processes are extremely efficient separation processes, generally without phase change and thus enabling a significant reduction in energy consumption, which use selective membranes, in which the feed flow is tangential to the membrane or to the membranes.

It has been demonstrated, moreover, that such a process makes it possible to obtain better performance levels than end-of-line treatments, where conventionally the aim is to use membrane processes, for instance the treatment of effluents using reverse osmosis in order to re-use the water and the dehydration of solvents by pervaporation, either for optimizing or completing distillation, or for reducing energy consumption or for obtaining the pure solvent. Moreover, the system according to the invention is more compact than the conventional separation systems, and has greater operational flexibility on the industrial level, due to the modular structures, and also offers lower maintenance costs since the membrane systems do not comprise moving parts.

A first subject of the present invention is thus a process for producing ketones or aldehydes obtained by condensation followed by dehydration and hydrogenation of ketones or aldehydes in a reactor, characterized in that said process comprises at least one step of partial elimination of water carried out by at least one membrane pervaporation module, fed tangentially and installed laterally to said reactor and operating in a loop, so as to partially dehydrate a fraction exiting the reactor and to recycle the dehydrated concentrate to said reactor.

The invention thus relates to a process for optimizing the production of ketones or aldehydes obtained by condensation followed by dehydration and hydrogenation of ketones and aldehydes in a reactor. According to the process of the invention, it is possible to use various types of ketones or of aldehydes in the reaction medium. The process targets in particular the obtaining of ketones or aldehydes containing an even number of carbon atoms, obtained by condensation followed by dehydration and hydrogenation of ketones or aldehydes.

Preferably, the reaction for condensation, dehydration and hydrogenation of the ketones or aldehydes is carried out in a single reactor.

Pervaporation is defined as an effective combination of permeation through membranes, followed by evaporation. Transport by pervaporation is usually described by means of the solution-diffusion model. The steps are: preferential sorption of the components at the interface of the membrane in contact with the liquid feed, differentiated diffusion through the membrane owing to the concentration gradients, and, finally, desorption in the form of vapor, on the other side of the membrane, maintained at low pressure. The first two steps correspond to the permselectivity of the membrane.

For the purpose of the invention, the term "pervaporation module" is intended to mean a tank comprising one or more pervaporation membranes. The pervaporation modules generally comprise planar membranes, mounted on metal supports, forming leaktight plates, spaced out so as to have the waste flow on one side and the permeate flow, such as the vapor, on the other; these plates communicate through collectors located opposite the feed for the discarded stream.

The pervaporation membranes are classified according to the nature of the separation to be studied. Hydrophilic membranes are particularly used for removing the water from solutions also containing organic compounds. These membranes are typically composed of polymers, the glass transition temperatures of which are above ambient temperature. Polyvinyl alcohol is an example of a hydrophilic membrane material. The pervaporation preferentially uses a membrane consisting of polymers having a glass transition temperature above ambient temperature. The membrane may consist of polyvinyl alcohol.

The permeability of the membranes of the invention can be between 500 and 2000 ml/h·m$^2$, preferably between 750 and 1500 ml/h·m$^2$, in the context of the process according to the present invention.

Those skilled in the art are perfectly familiar with the use of porous or nonporous hydrophilic membranes for dehydrating oxygenated organic compounds such as MIBK. Patents U.S. Pat. No. 4,910,344, CA 2196478, EP 496090, U.S. Pat. No. 4,935,144, EP 496090, EP 381477 and U.S. Pat. No. 5,139,677 are examples of implementations which concern the concentrating or the removing of water from aqueous organic solutions by pervaporation.

As shown in the scheme in FIG. 1, the reactants, such as ketones or aldehydes, in particular acetone (1) and hydrogen (2), are brought to the reactor (3). The stream (4) exiting the reactor (3) is conveyed predominantly to purification systems (8), in particular distillation systems, and a small part of this stream (5) is diverted to a membrane pervaporation module (6), where the water is partially removed (11). The partially dehydrated stream (7) is conveyed back to the reactor (3). The ketones or aldehydes produced and exiting the purification systems (8) are recovered by the means (10); while the ketones or aldehydes which have not reacted can be brought back to the reactor (3).

It is in particular preferable for the degree of reflux of stream (5) brought to the membrane pervaporation module (6) to be between 20% and 40% of the total exiting stream (4), exiting the reactor (3).

It is also preferable for the concentration of water in the reaction mass of the reactor to be maintained between 2% and 4% by weight. A reduction in the concentration of water in the reaction mass of between 0.5% and 2% by weight is in particular obtained.

The temperature in the membrane pervaporation modules can be between 70 and 90° C. The absolute pressure in the pervaporation modules can range between 5 and 7 kPa. This pressure corresponds to the pressure on the permeate side of the membranes.

The process of the invention can absolutely comprise several membrane pervaporation modules, mounted in series, in such a way that the solution is gradually dehydrated from the first to the last module. It is in particular preferred to use three modules mounted in series.

Thus, for example, for temperatures of between 100 and 150° C. and pressures of between 500 and 2000 kPa, a pump draws up a side stream, the flow rate by mass of which is between 20% and 50% of the flow rate by mass exiting the reactor, feeding an economizer device and reducing the temperature of this stream, which is between 100 and 150° C., to a module feed temperature of between 70 and 90° C. The pervaporation module feed, by weight, is composed of approximately 3% to 5% of water and 95% to 97% of organic components. The cooling liquid, in normal operation, is the partially dehydrated, discarded stream, at the exit of the final module of the membrane assembly at a temperature of between 70 and 90° C., and, at the start-up, is the water from the cooling tower.

Thus, the first pervaporation module is fed at a temperature of between 70 and 90° C. in order to begin the permeation of the mixture. The stream discarded in the first module, at a temperature below the ideal temperature, feeds a heat exchanger, using the vapor as heating means in order to ensure that the second module is also fed at a temperature of between 70 and 90° C.

In the same way as for the first module, the permeation of the permeate mixture continues in the second module and the stream discarded, also obtained at a temperature below the ideal temperature, is directed to the second heat exchanger, using the vapor as heating means in order to ensure that the third module is also fed at a temperature of approximately 70 to 90° C.

The final stream discarded, which is dehydrated by approximately 1% by weight, and is at a temperature of between 70 and 80° C., feeds the economizer device and cools the feed stream, as described above, being heated to a temperature of between 95 and 145° C. before returning to the reactor.

The permeation surface of each of the modules can range between 20 and 150 m$^2$, in particular between 40 and 60 m$^2$. The membranes can be installed in a tank operating at an absolute pressure between 5 and 7 kPa.

The pressure indicated can be obtained by means of a vacuum pump, installed at the output of the stream of permeate in the vapor state, requiring a condenser, fed with a solution of brine, making it possible to obtain water with a low concentration of acetone or aldehyde. The installation of a second condenser after the vacuum pump is necessary for obtaining a virtually pure acetone or aldehyde, which can be recycled to the process.

A subject of the present invention is also a device, such as those conventionally used for producing ketones or aldehydes, comprising at least one reactor (3) and a means for conveying the stream (4) exiting the reactor (3) in order to recover the ketones or aldehydes produced, and a means for conveying a side stream (5) exiting the reactor (3) to at least one membrane pervaporation module (6), and a means for conveying the resulting dehydrated concentrate (7) to said reactor (3).

The few examples which follow are simply by way of illustration and should not limit the scope of the invention.

BRIEF DESCRIPTION OF THE DRAWING

FIG. 1 shows and example of an apparatus for conducting the process as described herein, comprising a reactor (3) and a means for conveying the stream (4) exiting the reactor (3) to recover the ketone/aldehyde produced, and a means for conveying a side stream (5) exiting the reactor (3) to at least one membrane pervaporation module (6), and a means for transferring the resulting dehydrated concentrate (7) to said reactor (3).

EXPERIMENTAL SECTION

Example 1

A device similar to that in FIG. 1, comprising a membrane pervaporation module using a Sulzer PVAP 2256 membrane, is fed with the following composition:
water: 4.1
acetone: 85.2
MIBK: 10.7

With a reactor operating at 60° C., and considering 1% dehydration, a permeate (exiting flow) comprising 74.5% by weight of water, 25.5% of acetone and 0% by weight of MIBK is obtained; with a permeability of 1000 ml/h·m² of the operating membrane. The pressure on the permeate side of the membrane is 6 kPa.

On the basis of the results of the test, the impact of the use of the membrane pervaporation module on the reaction kinetics was evaluated in the absence and in the presence of a degree of reflux to the pervaporation module; the results are the following:

TABLE 1

|  | Comparative example | Example according to the invention |
|---|---|---|
| Degree of reflux (%) | 0 | 25 |
| MIBK production (tonne/day) | 100 | 120 |
| Water exiting the reactor (%) | 4.2 | 3.4 |

An increased reaction yield and a large increase in MIBK productivity are thus observed.

Example 2

An experiment was carried out using 3 membrane pervaporation modules, mounted in series, in such a way that the solution is gradually dehydrated from the first to the third module.

Acetone and hydrogen are introduced into the reactor for the purpose of obtaining MIBK.

From the stream exiting the reactor (4), a pump draws off a side stream (5), the flow rate by mass of which is equal to 35% of the flow rate by mass of the stream exiting the reactor (3).

The side stream (5) feeds an economizer device, thus reducing the temperature of this stream to 80° C. The cooling liquid, in normal operation, is the stream (7) discarded from the membrane assembly, at a temperature of 75° C. At the start-up, the cooling liquid is the water from the cooling tower.

Thus, the side stream (5) feeds the first pervaporation module so as to begin the permeation of the permeate mixture. The stream discarded in the first module, at a temperature of 72° C., feeds a heat exchanger in order to ensure that the second module is also fed at 80° C.

In the same way as for the first module, the permeation of the permeate mixture continues in the second module and the discarded stream, obtained at 74° C., is directed to the second heat exchanger, in order to ensure that the third module is also fed at 80° C.

The heating of the discarded streams in the exchangers described is carried out by feeding each of the heat exchangers described with saturated vapor.

The final discarded stream (7), correctly dehydrated, at a temperature of 75° C., feeds the economizer device and cools the feed stream for the first module, as described above, being heated to a temperature of between 95 and 145° C. before returning to the reactor.

The three pervaporation modules envisioned for carrying out the invention consist of planar membranes mounted on metal supports, constituting leaktight plates, spaced out so as to have the waste flow on one side and the permeate flow, such as the vapor, on the other, communicating through collectors located opposite the feed for the discarded stream. The membranes are installed in a tank operating at an absolute pressure of 6 kPa.

The pressure indicated is obtained using a vacuum pump, installed at the output of the stream of permeate in the vapor state, requiring a condenser, fed with a solution of brine, making it possible to obtain water with a low concentration of acetone. The installation of a second condenser after the vacuum pump is necessary for obtaining a virtually pure acetone, which can be recycled to the process.

A large increase in MIBK productivity is observed when a fraction of the stream exiting the reactor is brought to the pervaporation modules.

The invention claimed is:

1. A process for production of a ketone or aldehyde, the process comprising:
   (a) condensing a starting acetone/ketone or aldehyde followed by dehydrating and hydrogenating in a reactor to form a reaction mixture comprising water;
   (b) diverting a fraction of the reaction mixture exiting the reactor to at least one membrane pervaporation module, connected by a loop to said reactor;
   (c) partially eliminating water from the diverted reaction mixture in said membrane pervaporation module; and
   (d) recycling said dehydrated concentrate to said reactor.

2. The process as defined by claim 1, comprising production of methyl isobutyl ketone (MIBK) from acetone, or butanal from acetaldehyde.

3. The process as defined by claim 1, wherein the water in the reaction mixture in the reactor is maintained at from 2% to 4% by weight.

4. The process as defined by claim 1, wherein a reaction feed stream introduced to the membrane pervaporation module has a degree of reflux from 20% to 40%.

5. The process as defined by claim 1, comprising reducing the water in the reaction mixture by from 0.5% to 2% by weight.

6. The process as defined by claim 1, wherein said at least one pervaporation module comprises at least one hydrophilic membrane.

7. The process as defined by claim 6, wherein said at least one membrane of said at least one membrane pervaporation module comprises at least one polymer having a glass transition temperature above ambient temperature.

8. The process as defined by claim 1, wherein the membrane of said at least one membrane pervaporation module comprises polyvinyl alcohol.

9. The process as defined by claim 6, wherein said at least one membrane has a permeability from 500 to 2,000 ml/h·m².

10. The process as defined by claim 9, wherein said at least one membrane has a permeability from 750 to 1,500 ml/h·m².

11. The process as defined by claim 1, including a plurality of membrane pervaporation modules mounted in series.

12. The process as defined by claim 1, wherein said at least one membrane pervaporation module has a temperature from 70 to 90° C.

13. The process as defined by claim 1, wherein said at least one membrane pervaporation module has an absolute pressure from 5 to 7 kPa.

14. Apparatus for conducting the process as defined by claim 1, comprising a single reactor (3) and a means for conveying the stream (4) exiting the reactor (3) to recover the ketone/aldehyde produced, and a means for conveying a side stream (5) exiting the reactor (3) to at least one membrane pervaporation module (6), and a means for transferring the resulting dehydrated concentrate (7) to said reactor (3).

15. Apparatus as defined by claim 14, comprising 3 membrane pervaporation modules.

\* \* \* \* \*